United States Patent [19]
Fabricant et al.

[11] Patent Number: 4,722,887
[45] Date of Patent: Feb. 2, 1988

[54] PHASE PARTITION SEPARATION OF SPERM BASED ON SEMINOLIPID EXPRESSION

[75] Inventors: Jill D. Fabricant, Houston, Tex.; James D. Willett, Rockville, Md.

[73] Assignee: Biosyne Corporation, Houston, Tex.

[21] Appl. No.: 943,685

[22] Filed: Dec. 19, 1986

[51] Int. Cl.$^4$ .................. A01N 1/02; A61K 35/52; B01D 15/08
[52] U.S. Cl. ........................... 435/2; 435/7; 210/635; 424/85; 424/105
[58] Field of Search ............... 435/2, 7; 424/85, 105; 210/635; 530/852

[56] References Cited

U.S. PATENT DOCUMENTS

| | | | |
|---|---|---|---|
| 4,191,749 | 3/1980 | Bryant | 435/2 |
| 4,448,767 | 5/1984 | Bryant | 435/2 |

OTHER PUBLICATIONS

Erickson and Glass, Functional Differences Between Sperm Bearing the X or Y Chromosome, Prospects for Sexing Mammalian Sperm, 1982, pp. 201-223.
Kaneko, "Separation of Human X and Y Bearing Sperm Using Percoll Density Gradient Centrifugation", Fertility and Sterility, vol. 40, No. 5, Nov. 1983, pp. 661-665.
Gledhill, "Control of Mammalian Sex Ratio by Sexing Sperm", Fertility and Sterility, vol. 40, No. 5, Nov. 1983, pp. 572-574.
Albertson, "Separation of Particles and Macromolecules by Phase Separation Endeavour", vol. 1, No. 2, 1978, pp. 69-74.
Walter et al., "Surface Differences Between Erythrocytes from Arbitrarily Chosen (Presumably Hematologically Normal) Individuals Detected by Cell Partitioning", Biochemical and Biophysical Research Communications, vol. 120, No. 1, Apr. 1984, pp. 250-255.
Fisher, "Cell Separations and Subfractionations by Countercurrent Distribution in Two Polymer Phase Systems Depend on Non Equilibrium Conditions", Biochem. and Biophys. 801 (1984), pp. 111-116.
Walter et al., "Detection of Surface Differences Between Two Closely Related Cell Populations by Partitioning", Biochem. and Biophys. 855 (1986) pp. 8-15.
Sharpe et al., "Studies of the Growth of Human Bone Derived Cells in Culture Using Aqueous Two-Phase Partition", Bioscience Reports vol. 4 (1984) pp. 415-419.
Sharpe, "Use of Aqueous Two-Phase Partition to Detect Cell Surface Changes During Growth of Dictoystelium Discoideum", J. Cell Science, vol. 75, 1985, pp. 339-346.
Sharpe, "Synthesis and Application of a Polyethylene Glycol-Antibody Affinity Ligand for Cell Separations in Aqueous Polymer Two-Phase Systems", Analytical Biochemistry, vol. 154, pp. 110-117 (1986).
Hammerstedt, "Potentials of Physical and Biochemical Separation Methods", 1982, pp. 169-175.
Hoppe, "Reacting Mouse Sperm with Monoclonal H-Y Antibodies Does Not Influence Sex Ratio of Eggs Fertilized in Vitro", Journal of Reproductive Immunology 6, 1984, pp. 1-9.
Schmell, "Identification of Mammalian Sperm Surface Antigens", Journal of Reproductive Immunology, vol. 4, 1982, pp. 91-106.
Lingwood, "Tissue Distribution of Sulfolipids in the Rat", Can. J. Biochem. vol. 59, 1981, pp. 556-563.
Lingwood, "The Preparation of Rabbit Antiserum Specific for Mammalian Testicular Sulfogalactoglycerolipid", Journal of Immunology, vol. 124, No. 2, Feb. 1980, pp. 769-774.
Lingwood, "Localization of Sulfatoxygalactosylacylalkylglycerol", Journal of Cell Biology, vol. 89, 1981, pp. 621-630.
Smith, "Rapid Communication", Journal of Experimental Zoology, vol. 225, 1983, pp. 157-160.
Myles, "Surface Domains of the Guinea Pig Sperm Defined with Monoclonal Antibodies", vol. 23 (1981), pp. 433-438.
Peterson, "Rapid Communication", Journal of Experimental Zoology, vol. 223 (1982), pp. 79-81.
Schmell, "Identification of Mammalian Sperm Surface Antigens", Fertility and Sterility, vol. 37, No. 2, Feb. 1982, pp. 249-257.
Shirley, "Enrichment of Sulfogalactosylalkylacylglycerol", Can. J. Biochem., vol. 58, 1980, pp. 1230-1239.
Nicholson, "The Sperm Membrane", Prospects for Sexing Mammalian Sperm, 1982, pp. 42-47.
Reproduction Research Information Services, "Bibliography on Separation of X and Y Spermatozoa", vol. 32, No. 4, pp. 326-328.

*Primary Examiner*—Ernest G. Therkorn
*Attorney, Agent, or Firm*—Iver P. Cooper

[57] ABSTRACT

Male- and female-determining sperm are separated by polymeric phase partition chromatography, based on differential expression of a sulfoglycolipid. In a preferred embodiment, a mobile phase comprises a polymer derivatized with a sulfoglycolipid-binding protein, such as an antibody directed against the sulfoglycolipid. The sulfoglycolipid is preferably SGG.

9 Claims, No Drawings

PHASE PARTITION SEPARATION OF SPERM BASED ON SEMINOLIPID EXPRESSION

BACKGROUND OF THE INVENTION

This invention relates to the control of the sex of the offspring of mammals by the separation of male-(Y) and female-(X) determining sperm.

Any separation technique, to be effective, must be dependent on some phenotypic difference between X- and Y-sperm Suggested distinctions include fluorescence of the Y-chromosome, weight, density, size, adherence to Sephadex, motility in albumin, pH, surface charge, cell surface antigens, and enzymatic and hormonal environment. Erickson and Glass, *Functional Differences Between Sperm Bearing the X- or Y- Chromosome, in PROSPECTS FOR SEXING MAMMALIAN SPERM* (1982). For example, Kaneko, et al., Biochem. & Biophys. Res. Commun., 124: 950 (1984) suggests that X- and Y-bearing sperm may differ in cell surface charge as a result of differences in cell surface sialic acid content.

Considerable skepticism exists as to whether a successful separation scheme is even possible. Gledhill, Fertility and Sterility, 40: 572 (1983). Nonetheless, many patents have been issued to workers in this field. Bovenkamp, U.S. Pat. No. 3,687,806; Ericsson, U.S. Pat. No. 4,009,260; Hancock, U.S. Pat. No. 4,085,205; Bhattacharya, U.S. Pat. No. 4,155,831; Lawson, U.S. Pat. No. 4,276,139 and U.S. Pat. No. 4,225,405; Lang, U.S. Pat. No. 4,083,957; Shrimpton, U.S. Pat. No. 3,894,529 and U.S. Pat. No. 4,327,177; Adair, U.S. Pat. No. 4,362,246.

Albertsson generally teaches that polymer phase partition chromatography may be used to separate cells. He broadly suggests that the system may be designed so that cells are separated according to electrochemical, hydrophobic or biospecific surface properties. Albertsson, Endeavor, 1: 69 (1978). Walter and Krob, Biochem. & Biophys. Res. Commun., 120: 250 (1984) detected differences in membrane surface properties of erythrocytes by partitioning in dextran-poly(ethylene glycol) aqueous phase systems subject to countercurrent distribution. An improvement in their methodology was reported in Cell Biophysics, 6: 253 (1984). See also Fisher and Walter, Biochem. & Biophys. Acta, 801: 106 (1984); Walter and Krob, Biochem. & Biophys. Acta, 855: 8 (1986). Sharpe, et al., Bioscience Repts. 4: 415 (1984) partitioned human bone cells in the same two-phase system, obtaining two cell populations with different growth rates. Sharpe and Watts, J. Cell Sci., 75: 339 (1985) used aqueous two phase partition to detect changes in the cell surface properties of *D. discoideum* amoebae.

Immunoaffinity partitioning was explored by Sharpe, et al., Anal. Biochem. 154: 110 (1986), who used a two-phase dextran/PEG system in conjunction with PEG-bound antibody. The antibody "dragged" the antigen into the PEG-rich phase, thus accentuating the partitioning of the antigen achieved by the two-phase system alone.

Hammerstedt, in Prospects for Sexing Mammalian Sperm 169 (1982) speculates that polymer phase partition chromatography could be applied to the separation of sperm if a differentiating property could be identified.

Separation by immunological means has been suggested. Bryant, U.S. Pat. No. 4,448,767. However, for this method to succeed, one must develop an antibody against a cell surface marker for an X- or Y-determining sperm. McCormick, Infertility, 5(3): 217–227 (1983) exposed sperm to polyclonal antibodies against the H-Y antigen, which is expressed by male sperm. Monoclonal antibodies were similarly used when they became available. However, the efficacy of this method has been questioned. Hoppe and Koo, J. Reprod. Immunol., 6: 1–9 (1984).

Antibodies have been prepared against sperm surface antigens. Smith, et al., J. Exper. Zoology, 225: 157 (1983); Myles, et al., Cell, 23: 433 91981); Peterson, et al., J. and Sterility, 37: 249 (1982); Schmell, et al., J. Reprod. Immunol., 4: 91 (1982). In particular, antibodies have been prepared against the sulfogalactoglycerolipid found in mammalian testes. Lingwood, et al., J. Immunology, 124: 769 (1980); Lingwood and Schactiter, J. Cell Biol., 89: 621 (1981); Lingwood, et al., Can. J. Biochem., 59: 556 (1981); Shirley and Schacter, Can. J. Biochem., 58: 1230 (1980). However, these antibodies have not been used in separating X- and Y-sperm.

It has also been suggested that cryptic spermal antigens may be exposed by treatment with pronase, trypsin, or other enzymes, though care must be taken to ensure that the sperm can still recognize and bind specifically to oocytes. See Nicholson, The Sperm Membrane, in PROSPECTS FOR SEXING MAMMALIAN SPERM (1982) at 45.

SUMMARY OF THE INVENTION

The sperm surface is inherently asymmetric both in terms of its lipid composition (Phosphatidyl choline and cholesterol for example) and glycoprotein and glycolipid constituents. Lectins bind to complex carbohydrates, including glycolipids and glycoproteins. Mammalian sperm surfaces have on the order of 10,000,000 lectin binding sites/cell. Most of these are found on the head region of the sperm cell. Considerable DNA and histone synthesis occurs in spermatocytes but mature sperm show no evidence of mRNA synthesis, making unlikely late stage haploid surface expression of sperm surface components. Any difference existing in cell surface characteristics between X and Y bearing mature sperm must be set at some time before or during mid to late spermiogenesis. Therefore key elements for consideration as targets for cell surface dependent separation attempts of X and Y bearing sperm are unique sperm surface constituents present in the early stages of spermiogenesis and retained by mature sperm or which show indications of being present in modified form in mature sperm. It is noted that the number of available binding sites on ejaculated sperm is reduced by 30–50% over that detectable on differentiating spermatogenic cells. This is not surprising considering the marked change in environment experienced by these cells at these two separate stages of development. Any use of cell surface ligand-external ligand specific large molecule interactions is more likely to be successful if run on enzyme pretreated sperm or sperm washed to remove adhering extracellular proteins. These materials are preferably retained for recombination with the separated sperm to promote successful fertilization.

Our technique is to separate X sperm from Y sperm by partition chromatography, based on differential haploid expression of a sulfoglycolipid, particularly sulfogalactosylacylalkylglycerol (SGG).

The term sulfatide has been used to described lipids containing esterified sulfate, but excluding steroid sulfates. Haines, Prog. Chem. Fats Lipids, 11: 299 (1971). "SGC", sulfogalactosyl ceramide is the classic sulfatide. A novel sulfatide, a sulfogalactoglycerolipid ("SGG") was discovered in rat, boar, and guinea pig tests. Structural analysis revealed that in these animals, it was predominantly 1-0-palmityl-2-0-palmitoyl-3-beta-[3'-sulfogalactosyl]-glycerol, which may more generally be written as 1-0-alkyl-2-0-acyl-3-beta-(3'-sulfogalactosyl)-glycerol. Kornblatt, et al., Can. J. Biochem., 52: 689 (1974).

The seminolipid upon which our separations hypothesis is based, SGG, is a unique, sperm surface constituent, and is not known in other cell type. The molecule most closely related structurally to SGG is the myelin sulfogalactolipid, SGC. Though showing some cross-reactivity with some antibodies, specific antibodies to each are known. SGG and SGC are acidic, highly anionic lipids and are known to be associated with basic proteins. This has been demonstrated most extensively in the studies of the myelin sulfogalactolipid, SGC and its association with myelin basic protein, MPB. These lipids are thought involved in ion transport phenomena in their respective membranes, and SGG has been implicated in sperm capacitation and fertilization.

We believe that as SGG is a sperm unique membrane constituent that it reflects either directly or indirectly the function of the Y-chromosome. The levels of SGG present rat spermatozoa are one micromole per gram wet weight of cells. The levels of SGG increase in spermatocytes at a greater rate than that of any other lipids which lends credence to the postulate that these lipids have a special function in sperm. See for example Farooqui A. A.: "Metabolism and Role of Sulfolipids in Mammalian Tissues" Int'l. J. Biochem., 9: 709–716, (1978), Farooqui A. A. and Horrocks C. A., Mol. Cell Biochem., (1985) 66: 87–95. These lipids are important in spermatogenesis, cell-cell interactions, and in differentiation; Schachter H., Roseman, S. In: Lennarz W. J. (ed), "Biochemistry of Glycoproteins and Proteoglycans, Plenum Publ. Corp. N.Y. (1980), pp 85-160.

In support of this hypothesis, sterol sulfatases are found to show sex linked quantitative differences with the levels in samples from males being two to three fold greater than in females. See; Rabe T., Kiesel. L., Racke G. Runnebaum B. J. Steroid Biochem., (1984), 20: 627–32. These are enzymes which hydrolyze sterol sulfates in the same manner as aryl sulfatases hydrolyze SGG. Both substrates are believed to play critical functions in sperm capacitation and fertilization. Though indirect, the direct evidence that quantitative sex-linked differences are shown in enzymes associated with the fundamental metabolic pathways of substrates whose physiological functions are associated, lends support to the expectation that SGG itself will show sex-linked quantitative differences, with Y bearing sperm showing greater amounts of this lipid component than X.

The phase system must be one which does not impair the viability or competency of the sperm. Polymeric phase systems are known which are mild toward cells and subcellular particles. Polyhydrated polymers, such as dextran, are preferred.

If a single partitioning does not result in a complete separation of X- and Y-sperm, the enriched fractions may themselves be subjected to further partition chromatography.

It should be emphasized that the method proposed herein does not require that the seminolipid be present on only one of the two types of sperm. Rather, a quantitative difference is sufficient.

The partition chromatography method of the present invention may be combined with other methods used to separate sperm.

DETAILED DESCRIPTION OF THE INVENTION

Presented below is a hypothetical example of a complete protocol for an immunopartitioning of X- and Y-bearing sperm based on differential surface expression of SGG. It will be understood that some further optimization may be necessary to obtain the desired results. Possible modifications in the preferred method are discussed immediately following the hypothetical example.

Example

Phase partition is a method of separating macromolecules, cell particles and cells according to their surface properties. Phase partition involves the selective distribution of cells or cell particles between two immiscible aqueous liquid phases. Such phases are created by mixing two water soluble polymers in water. This is a very general phenomenon as it is the exception rather than the rule that solutions of two separate polymers are miscible. Two polymers must be extremely similar in their properties for their solutions to be miscible. Aqueous solutions of dextran and poly(ethyleneglycol) when mixed, form two phases. Such systems are mild towards biological particles and cells. By selecting the characteristics of the polymers used one can effect separations based on electrochemical, hydrophobic and biospecific surface properties.

Our separations are preferably carried out using two aqueous polymeric phases, preferably dextran and poly(ethyleneglycol), PEG, the latter containing an antibody to the sperm surface lipid, sulfatoxygalactosylacylalkylglycerol, SGG.

To prepare the antibody, the lipid is isolated from bovine sperm or testis by extraction of tissue or cell homogenates in cold buffered PBS (phosphate-buffered saline, pH 7.8) with ethanol followed by 10 volumes of 2:1 chloroform/methanol, v/v. followed by 10 volumes of 1:1 chloroform/methanol, v/v. The lipid extracts are washed with 5 volumes of Folch upper phase, combined and concentrated in vacuo. The lipids are taken up in a minimum vol. of chloroform and placed on a Florasil column built in chloroform. The column is eluted with 10 column volumes of chloroform and then the sulfolipids are eluted with acetone. Pure SGG is obtained by preparative thin layer chromatography on silica-gel developed with chloroform/methanol/water, 65;25:4. The SGG band is removed, extracted into ethylacetate, conc. in vacuo and redissolved in 2:1 chloroform/methanol.

Rabbits are immunized with the purified SGG according to the procedure of C. A. Lingwood, R. K. Murray and H. Schacter, (1980), J. Immunol., 124,769–774. Liposomes are formed by dissolving 4 mg SGG, 16 mg lecithin and 40 mg cholesterol in 1.5 ml of ethanol and adding the solution slowly with stirring to 50 ml of water. Twenty mg of BSA in 20 ml water is added and the mixture left overnight at RT. The mixture is centrifuged at 13,000 xG for 60 min, the pellet resuspended in 20 ml water and separated into 1 ml fractions sealed in separate ampules and maintained at 4 degrees C.

Each rabbit receives the contents of one ampule i.v. two times a week for five weeks. Antibody levels are measured by complement fixation as described in Lingwood et. al. Antibody in the collected serum from the immunized rabbits is purified by precipitation of the immunoglobin fraction with 33% ammonium sulfate. The precipitate is redissolved in saline, dialyzed against 0.1M Tris-0.5M NaCl, and fractionated into IgM and IgG subclasses on Sephacryl S200 (Pharmacia) equilibrated with 0.1M Tris-0.5M NaCl, pH 8.0. Final purification of the SGG antibody is effected using the cholesterol/SGG immunoabsorbant procedure of Coulon-Morelec, Ann. Inst. Pasteur, Paris, 13: 37 (1967). The antibody, which remains in the lower phase when the cholesterol/SGG immunoadsorbent is dissolved in petroleum ether, is dialyzed against saline, adjusted to a volume of 1 ml and stored at −20 degrees C.

Preparation of PEG functionalized with the SGG specific antibody can be carried out in several ways, e.g., by the procedure of Sharp et. al. (Anal. Biochem., 154,110–117, 1986). PEG 1900, (Union Carbide) is converted to PEG-cyanuric chloride by the method of Abuchowski et al., J. Biol. Chem. 252, 3578-3581 (1977). To a solution of 7 mg SGG antibody in 0.1M borate buffer, pH 9 is added PEG-cyanuric chloride at a molar ratio of 3 PEG to every 1 lysine in the antibody. The reaction is carried out at room temperature for one hour. Derivatized antibody is separated from unreacted PEG by gel filtration on Bio-Cell P100 eluting with 20 mM NaCl and 10 mM sodium phosphate buffer, pH 7.8. PEG is also derivatized with mesylates of w-fatty acid t-butyl esters in pyridine. The purified derivatized polymer is converted to the free acid form by mild acid hydrolysis and the acid azide prepared from the corresponding acyl chloride in dimethoxyethane. Solutions of the PEG-long chain acid azide are added to the protein in aqueous buffer in the dark and PEG labeling of the protein affected by photolysis using a low pressure mercury lamp. The derivatized protein is purified by gel filtration chromatography as described above.

Phase separations are conducted using a 60 or 120 cavity thin layer counter current distribution apparatus. A neutral phase system is employed with 5.5% (w/w) dextran T500 (Pharmacia) and 5.5% (w/w) PEG, prepared as described, in 0.05M NaCl, 0.01M sodium sulfate and 0.001M phosphate buffer, pH 7.8. Separations are conducted at 4 degrees Centigrade with a 30 second shake time and an eight minute settling time. Sixty transfers are performed. Phosphate buffered saline is added to each cavity and the contents transferred to separate tubes. Separation between X and Y bearing sperm is accomplished in this manner.

Preparation of Sperm

Ejaculated sperm may be washed in dilute buffered detergent solutions to remove adsorbed surface materials without loss of viability or competency.

In one embodiment, the sperm are treated with trypsin or other proteolytic enzymes to expose deeper lying or cryptic antigens.

Preparation of Phase Polymers

While a variety of polymer combinations may be used in the phase partition chromatography of the sperm, the preferred polymers are dextran, polyethylene glycol (PEG), and aminohexyl-Agarose. A larger number of liquid polymer two phase systems are known. See Martin and Synge, Biochem. J., 35: 1358 (1941); Table 2.1 in Albertsson, PARTITION OF CELL PARTICLES AND MACROMOLECULES (2d ed. 1971). Polyphase systems have also been developed. See Table 2.2. Phase diagrams are given for selected phase systems at pages 261–313. A complete experimental procedure for a Dextran/PEG partitioning of mitochondria in a system employing countercurrent distribution is given in Albertsson's Appendix.

Preferably, the polymer is derivatized with a protein having an affinity for the seminolipid.

Without intending to limit the scope of the invention, the following binding proteins are suggested:

(a) myelin basic protein, which is known to be associated with a sulfogalactolipid in myelin.

(b) monoclonal antibodies which are directed against sulfomonogalactolipids. Such antibodies may be prepared by the method of Goujeft-Zalc, et al., J. Neurochem., 46: 425 (1986).

(c) monoclonal antibodies which react exclusively with SGG. These may be produced using SGG conjugated to glass beads in an in vitro antibody—producing system as taught by Eddy, et al., J. Immunol. Meth. 81: 137 (1985).

(d) monoclonal antibodies which bind sulfogalactolipids but not galactolipids. Liposomes containing SGG may be employed to generate these antibodies toward SGG according to the procedures of; Wassef, N. M., et al., Mol. Immunol. 21: 863-8 (1984). An antibody specific for the same epitope as present on SGG and SGC can be prepared in rabbits according to the procedure of Tocque, et al., J. Neurochem. 42: 1101-6 91984). This antibody is highly specific toward anionic sulfoglycolipids.

(e) other anion-binding proteins, such as those identified by Walkoff, et al., J. Clin. Invest., 76: 454 (1985).

Classical linkage techniques such as those described by Carraway K. L. and Koshland D. E. Jr. in Methods Enaymol. 2b: 616–623 (1972), are highly suited to the covalent binding of the myelin basic proteins as well as the various antibodies to the water soluble polymers chosen for these experiments. No prior chemical treatment is needed for aminohexyl-Agarose in this instance, but the Dextran and PEG require additional functionalization to generate the needed free amino or carboxyl groups this technique requires.

Suitably derivatized Agarose are also available using the procedures of Barker, et al., J. Biol. Chem., 247: 7135 (1972); and Kaplan F. and Hechtman P., Biochem. J., (1984) 217, 353–364. Procedures for inserting aminoethyl groups on hydroxyl containing polymers are described by Darmon, et al., Biochim. Biophys. Acta (1985) 817: 238–48.

Dextran sulfates and derivatized sulfates are preparable and the former are directly manipulable; see Sugawara I. and Ishizaka S., Microbiol. Immunol. (1984) 28: 831–9.

Classical protein linkages of enzymes to polymeric surfaces under conditions retaining the enzymatic activity in which the linkage agent used is cyanogen bromide may be made as taught by Warheed A. and Van Etten R. L., Int. J. Pept. Protein Res. (1985) 26: 362–72, Laidler P. M., Warheed A. and Van Etten R. L. (1985) ibid. 827: 73–83, and Darmen A. et al., Biochim, Biophys. Acta (1985), 817: 238-248.

Modifications of Dextran and Polyethyleneglycol (PEG) and other hydroxy containing polymers using mesylates of long chain omega-hydroxy fatty acid t-butyl esters will provide functionalized polymers readily convertible to the free long chain carboxylic acid that can be linked to a wide range of proteins using methods described previously. These functionalized polymers, in which the alkyl chain between the polymer and the free carboxyl function is variable in length from 4 to 24 carbon atoms, are ideally suited to functionalizations useful in photolabeling of proteins with these altered polymeric materials.

Separation of Sperm

At least two immiscible, water-soluble, polymeric phases are provided. A preferred polymer combination is dextran/PEG. Albertsson, Endeavor, 1: 69 (1977). Preferably, at least one of the polymeric phases is altered so as to enhance partitioning of the sperm on the basis of biospecific interactions with the exposed seminolipids. However, this invention is not so limited.

Thus, one polymer may be derivatized with SGG binding proteins, such as anti-SGG antibodies, so as to tend to retain Y bearing sperm.

In another but related approach, one polymer is derivatized with SGG or related lipids. Y bearing sperm, because of their higher expression of SGG, will also bear greater quantities of bound SGG-basic proteins (present originally or added later). These "complexed" sperm will tend to be retained in the SGG-derivatized polymer phase.

The lipids themselves will be isolated and purified as described by Jungalwala F. B., Koul O., Stoolmiller A., and Sapirstein, V. S. J. Neurochem., (1985), 45: 191-198. Modification of the lipids linked to the polymeric phases will be conducted using beta galactosidases, and homogeneous arylsulfatases. Preparation of these enzymes will be according to the procedures of Farooqui, A. A. and Horrocks, L. A., Neurochem. Pathol. (1984), 2: 189-218.

In a preferred embodiment, advantage is taken of the higher motility of Y bearing sperm by employing a stationary polymeric phase having a higher affinity for X bearing sperm and a mobile phase having a higher affinity for the more motile Y bearing sperm.

Besides actual modification of the phase polymers, it is possible to improve partitioning by adding other constituents which modify the ionicity or hydrophobicity of the phase, or which have a biospecific interaction with the seminolipid. The partition coefficient of the sperm in the selected phase system may be altered by judicious introduction of particular salts, as taught by Walter, in METHODS OF CELL SEPARATION, Vol. I, at 316-317 (1977). It may also be altered by the addition of small charged or uncharged molecules. Id., 322-324.

When the differences in surface properties between two species of a mixture are great enough, a single partitioning may result in an acceptable separation of the species between the phases. If the differences are subtle, one must use a multiple extraction technique such as countercurrent distribution. See Ito, TIBS 47 (February 1982); Sutherland and Ito, Anal. Biochem., 108: 367 (1980); Walter, in METHODS OF CELL SEPARATION, Vol. I, at 329-330 (1977). The use of countercurrent techniques is preferred.

Evaluating SGG Expression

A number of methods of assaying sulfolipids are known and may be of value in evaluating relative SGG expression on the X and Y bearing sperm. Murakami-Murofushi, et al., Anal. Biochem., 149: 480 (1985), Zalc, et al., Immunochem., 14: 775 (1977), Kean, J. Lipid Res., 9: 319 (1968).

We claim:

1. A method of separating a mixture of mature spermatozoa into a fraction enriched for X-bearing spermatozoa and a fraction enriched for Y-bearing spermatozoa, which comprises subjecting a mixture of spermatozoa to partition chromatography conditions, wherein the spermatozoa are partitioned under said chromatographic conditions by a plurality of immiscible polymeric phases, at least one phase preferentially binding a sulfoglycolipid and subsequently separating the phases.

2. The method of claim 1 in which the spermatozoa are first treated to expose the sulfoglycolipid.

3. The method of claim 1 in which the sulfoglycolipid is a sulfoxygalactosylalkylacylglycerol.

4. The method of claim 1 in which in at least one said phases, the polymer is derivatized with a protein which preferentially binds the sulfoglycolipid.

5. The method of claim 1 in which the protein is an antibody.

6. The method of claim 4 in which the protein is myelin basic protein.

7. The method of the claim 1, in which in at least one of the phases of a polyhydrated polymer-bound sulfoglycolipid is provided.

8. The method of claim 1 in which one phase is a stationary phase and another phase is a mobile phase, the X bearing sperm have a higher affinity for the stationary phase, and the Y bearing sperm have a higher affinity for the mobile phase.

9. The method of claim 1 in which one polymeric phase is formed by a dextran and another polymeric phase is formed by a polyethylene glycol.

* * * * *